(12) United States Patent
Schneider et al.

(10) Patent No.: US 7,957,789 B2
(45) Date of Patent: Jun. 7, 2011

(54) THERAPY DELIVERY SYSTEM INCLUDING A NAVIGATION ELEMENT

(75) Inventors: Mark D. Schneider, Mound, MN (US); Michael R. Neidert, Minneapolis, MN (US); Kenneth C. Gardeski, Plymouth, MN (US); Johnson E. Goode, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1200 days.

(21) Appl. No.: 11/322,393

(22) Filed: Dec. 30, 2005

(65) Prior Publication Data

US 2007/0164900 A1   Jul. 19, 2007

(51) Int. Cl.
*A61B 5/05* (2006.01)

(52) U.S. Cl. ......................... 600/424; 606/130

(58) Field of Classification Search .................. 600/433, 600/407, 422–424; 606/130
See application file for complete search history.

(56) References Cited

U.S. PATENT DOCUMENTS

| | | | |
|---|---|---|---|
| 4,905,698 A | 3/1990 | Strohl et al. |
| 5,042,486 A | 8/1991 | Pfeiler et al. |
| 5,391,199 A | 2/1995 | Ben-Haim |
| 5,443,489 A | 8/1995 | Ben-Haim |
| 5,558,091 A | 9/1996 | Acker et al. |
| 5,568,809 A | 10/1996 | Ben-Haim |
| 5,715,822 A | 2/1998 | Watkins et al. |
| 5,833,608 A | 11/1998 | Acker |
| 5,938,603 A | 8/1999 | Ponzi |
| 6,005,465 A | 12/1999 | Kronenberg et al. |
| 6,104,944 A | 8/2000 | Martinelli |
| 6,112,111 A | 8/2000 | Glantz |
| 6,185,448 B1 | 2/2001 | Borovsky |
| 6,213,995 B1 | 4/2001 | Steen et al. |
| 6,236,875 B1 | 5/2001 | Bucholz et al. |
| 6,241,671 B1 | 6/2001 | Ritter et al. |
| 6,253,770 B1 | 7/2001 | Acker et al. |
| 6,385,472 B1 | 5/2002 | Hall et al. |
| 6,427,314 B1 | 8/2002 | Acker |
| 6,470,207 B1 | 10/2002 | Simon et al. |
| 6,490,467 B1 | 12/2002 | Bucholz et al. |
| 6,491,699 B1 | 12/2002 | Henderson et al. |
| 6,493,573 B1 | 12/2002 | Martinelli et al. |
| 6,574,492 B1 | 6/2003 | Ben-Haim et al. |
| 6,580,938 B1 | 6/2003 | Acker |
| 6,589,163 B2 | 7/2003 | Aizawa et al. |
| 6,636,757 B1 | 10/2003 | Jascob et al. |
| 6,690,963 B2 | 2/2004 | Ben-Haim et al. |
| 6,701,179 B1 | 3/2004 | Martinelli et al. |
| 6,702,777 B2 | 3/2004 | Ben-Haim et al. |

(Continued)

FOREIGN PATENT DOCUMENTS

WO    WO9829055 A    7/1998

(Continued)

OTHER PUBLICATIONS

International Search Report, PCT/US2006/062150, Jul. 26, 2007, 8 Pages.

*Primary Examiner* — Tse Chen
*Assistant Examiner* — Vani Gupta

(57) ABSTRACT

An electromagnetic receiver assembly is included in a navigation element for a therapy delivery system. If the system is modular, the navigation element may be an insertable module thereof and/or include a lumen to receive another insertable module.

8 Claims, 8 Drawing Sheets

U.S. PATENT DOCUMENTS

| | | |
|---|---|---|
| 2002/0045816 A1 | 4/2002 | Atalar et al. |
| 2003/0052785 A1 | 3/2003 | Gisselberg et al. |
| 2003/0097064 A1* | 5/2003 | Talpade et al. ............... 600/434 |
| 2003/0114778 A1 | 6/2003 | Vilsmeier et al. |
| 2004/0097804 A1 | 5/2004 | Sobe |
| 2004/0097806 A1 | 5/2004 | Hunter et al. |
| 2005/0085715 A1 | 4/2005 | Dukesherer |
| 2005/0165301 A1 | 7/2005 | Smith et al. |
| 2005/0251031 A1* | 11/2005 | Smith ........................... 600/433 |
| 2005/0277889 A1 | 12/2005 | Neidert et al. |
| 2005/0288695 A1 | 12/2005 | Jenson et al. |

FOREIGN PATENT DOCUMENTS

| | | |
|---|---|---|
| WO | WO 99/43253 | 9/1999 |
| WO | WO 00/10456 | 3/2000 |
| WO | WO 01/80922 A2 | 11/2001 |
| WO | WO 02/089908 A1 | 11/2002 |
| WO | WO2005112836 A | 12/2005 |
| WO | WO 2005112836 A2 * | 12/2005 |

* cited by examiner

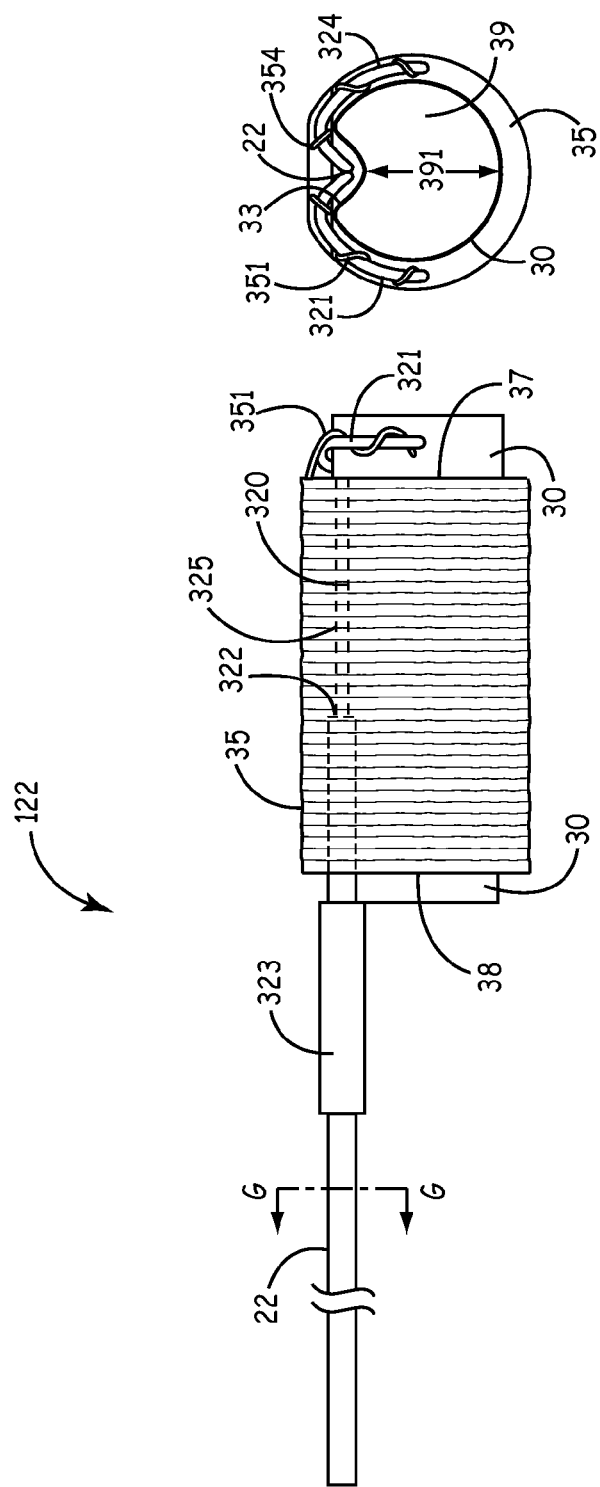

US 7,957,789 B2

THERAPY DELIVERY SYSTEM INCLUDING A NAVIGATION ELEMENT

TECHNICAL FIELD

The present invention pertains to medical therapy delivery systems and more particularly to therapy delivery systems that include a navigation element.

BACKGROUND

In recent years image guided navigation systems utilizing an electromagnetic source and electromagnetic detectors or receivers have been developed for minimally invasive surgical implantation procedures. The source, positioned external to a patient, sets up a magnetic field that induces a voltage in receivers mounted on a surgical instrument or delivery tool which has been inserted within a body of a patient disposed within the magnetic field. The voltage induced in each receiver is dependent upon a location and orientation of the respective receiver within the magnetic field. By sensing and processing current conducted from each receiver, a navigation analysis system can determine a location of each receiver with respect to one another and provide a visual map to aid an operator in navigating the instrument or tool to a target site within a body of a patient. An example of such an image guided navigation system is described in pre-grant patent publication US 2004/0097806, salient portions of which are hereby incorporated by reference.

If electromagnetic receivers are mounted directly onto a delivery tool, for example a guiding catheter, the receivers may either increase the profile of the tool or take up space within the tool that could otherwise be used to deliver therapeutic elements, for example, a medical device inserted through a lumen of the tool. Thus, it would be desirable to have a modular therapy delivery system wherein a navigation element including electromagnetic receivers can be included in the system for navigation purposes, and then removed from the system to increase system capacity for therapy delivery, for example, to open up a lumen for passage of a medical device therethrough, once the system has been navigated to an appropriate site. It would be further desirable that such a navigation element be constructed for maximum durability and to accommodate additional modules of the modular system.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIGS. 3A-B are a plan view and an end view of a receiver assembly for a navigation element according to some embodiments of the present invention.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention.

Figure 1A:
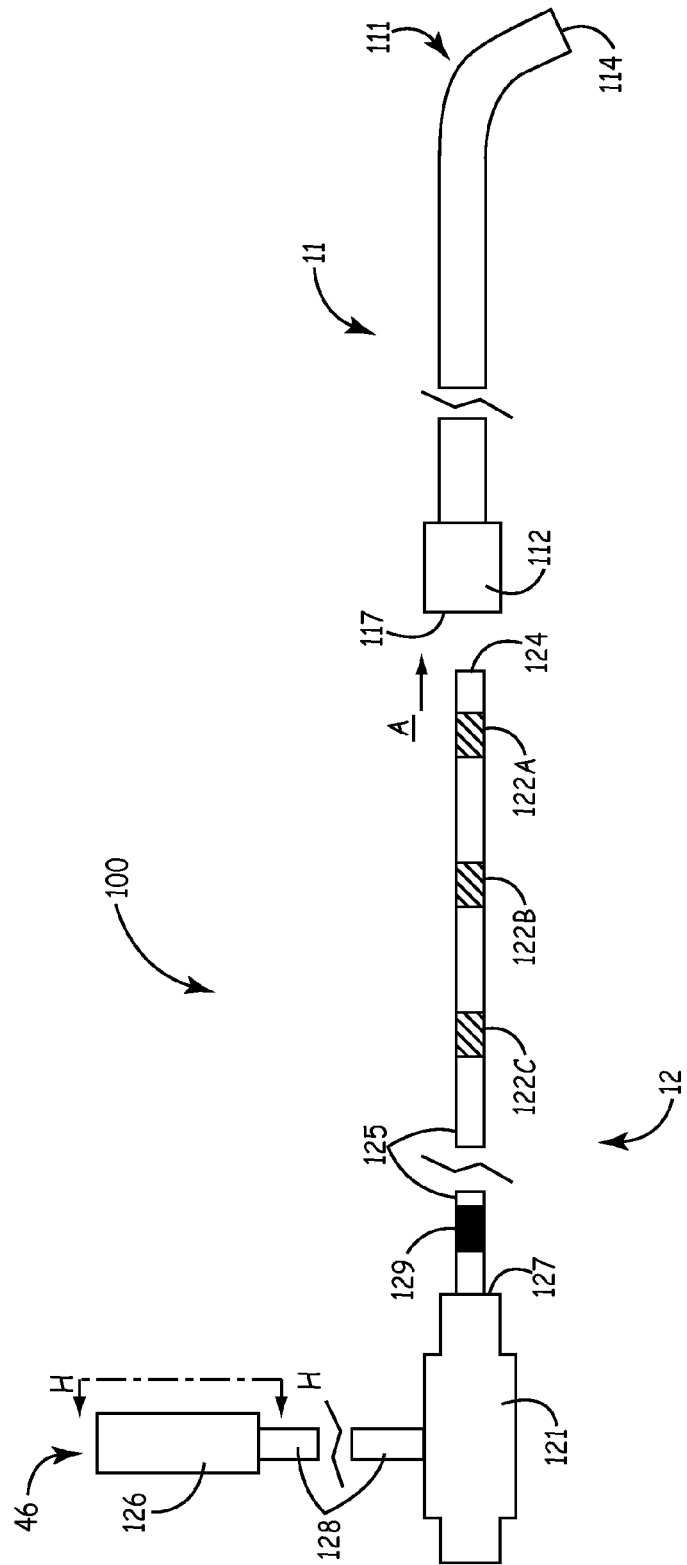
FIG. 1A is a plan view of a modular therapy delivery system depicting assembly thereof according to some embodiments of the present invention.
Figure 5A:
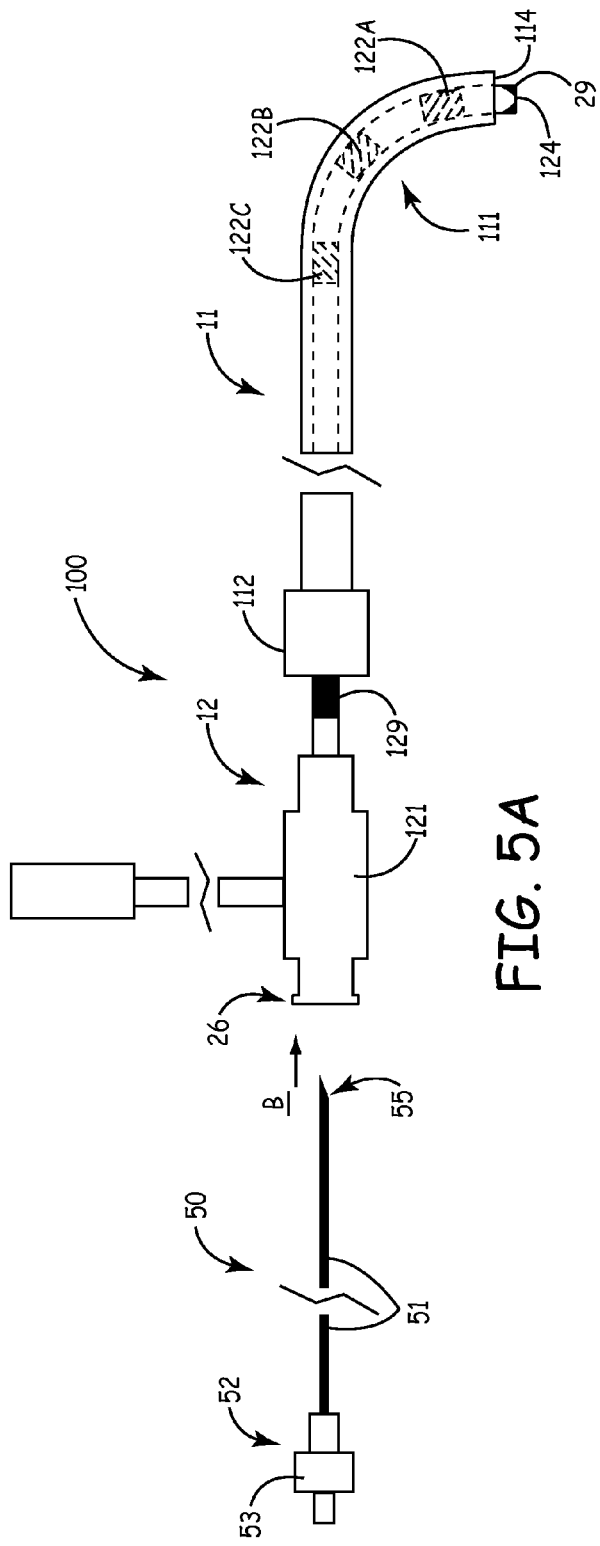
FIGS. 5A-B are plan views of the modular system shown in FIG. 1, further including another element and depicting assembly thereof according to further embodiments of the present invention.

FIG. 1A is a plan view of a modular therapy delivery system 100 depicting assembly thereof, per arrow A, according to some embodiments of the present invention. FIG. 1A illustrates system 100 including a catheter 11 and a navigation element 12 directed, per arrow A, for insertion at a proximal end 117 of catheter, to be slidingly received within a lumen thereof; navigation element 12 includes three electromagnetic receiver assemblies 122A, 122B and 122C that, once positioned within catheter 11, for example as shown in FIG. 5A, will aid an operator in navigating catheter 11 within a body of a patient to a target site, as previously described.

FIG. 1A further illustrates navigation element 12 including: an elongate body 125, to which receiver assemblies 122A, B, C are coupled, the most distal receiver assembly 122A being proximate to a distal end 124 of body 125; a hub 121 coupled to a proximal end 127 of body 125; and a connector 126 coupled to hub 121 via an insulated extension 128. According to the illustrated embodiment, current conducted from each receiver assembly 122A, B, C is transferred to an analysis component of a navigation system (not shown) via contacts 46 (FIG. 4) of connector 126; a current conduction pathway from each receiver 122A, B, C to connector 126 is described in greater detail below.

Figure 1B:
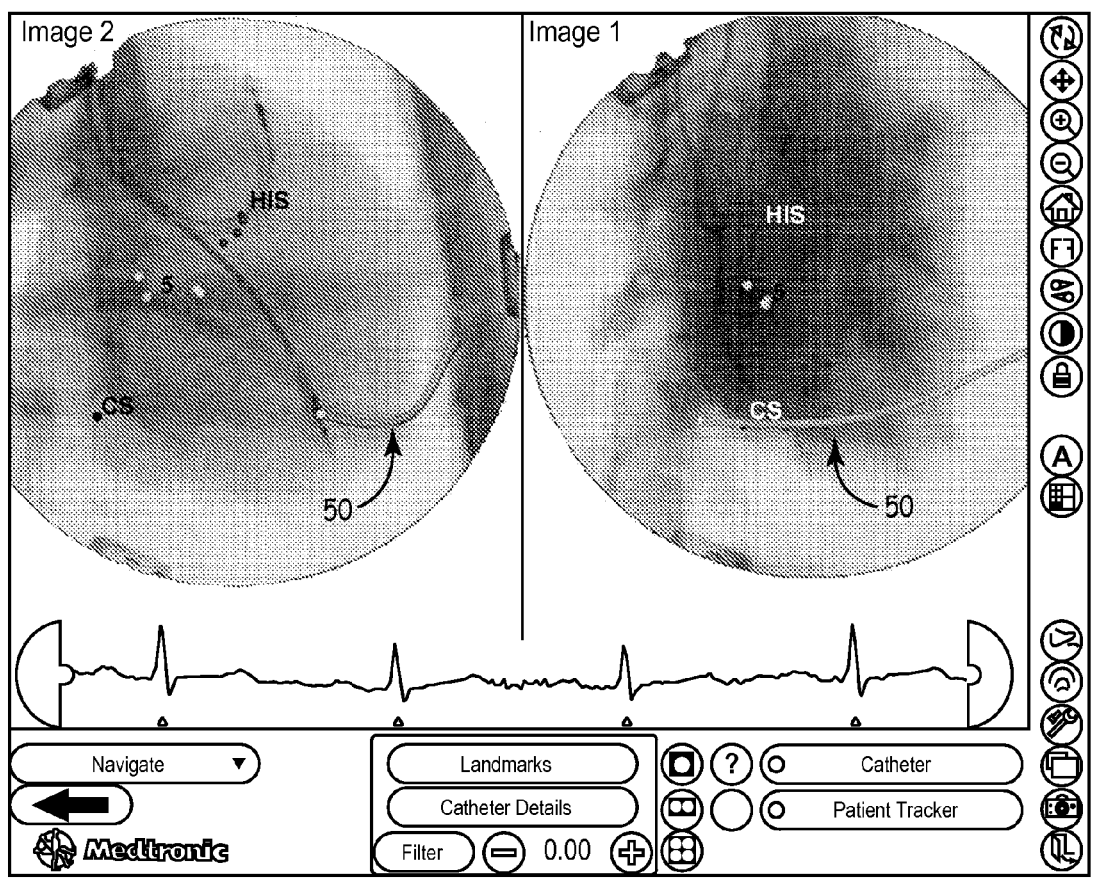
FIG. 1B is a screenshot provided by an exemplary navigation system.

FIG. 1B is an exemplary screenshot provided by a navigation system. An analysis component of the navigation system processes current signals from electromagnetic receiver assemblies, for example assemblies 122A, B, C, into location data, and combines the location data with fluoroscopic images. FIG. 1B illustrates an example of resulting images, often called virtual fluoroscopy, by which an operator maneuvering a catheter, in which a navigation element is inserted, for example element 12 in catheter 11, can track a location of the catheter without ongoing fluoroscopic guidance. In FIG. 1B, fluoroscopic images 1 and 2 are different perspective views of a heart in which the landmarks of the coronary sinus (CS) and the bundle of HIS are identified and on which catheter location data processed by the analysis system are overlaid. An interpolation between points that correspond to the location of the receiver assemblies results in splines 50, which represent a distal portion, for example approximately 10 centimeters, of the catheter at a first location; points adjacent to item number 5 represent previous locations of the catheter tip.

Referring back to FIG. 1A, a bend 111 formed in catheter 11, shown proximate to a distal end 114 thereof, may be useful for steering a distal end 114 of catheter 11 to the target site and may be pre-formed; alternately catheter 11 may be a steerable type wherein bend 111 is formed actively by an operator via control elements built into catheter 11. According to certain embodiments, catheter 11 has an outer diameter between 7 Fr and 12 Fr, and an overall length of system 100, when assembled, may range from approximately 5 inches to approximately 60 inches, depending upon a location of a target site inside a body with respect to an access site outside the body. Pre-formed and steerable catheters are well known to those skilled in the art.

It should be noted that navigation element 12 may be inserted, per arrow A, into catheter 11 either before or after catheter 11 has been inserted within a body of a patient, for example within the patient's venous system via percutaneous access. According to some embodiments of the present invention, navigation element 12 may be removed, once catheter 11 has been successfully navigated to a target site, to make way for delivery of a therapeutic or diagnostic agent through catheter, for example an implantable medical electrical lead or a biopsy instrument.

Figure 2:
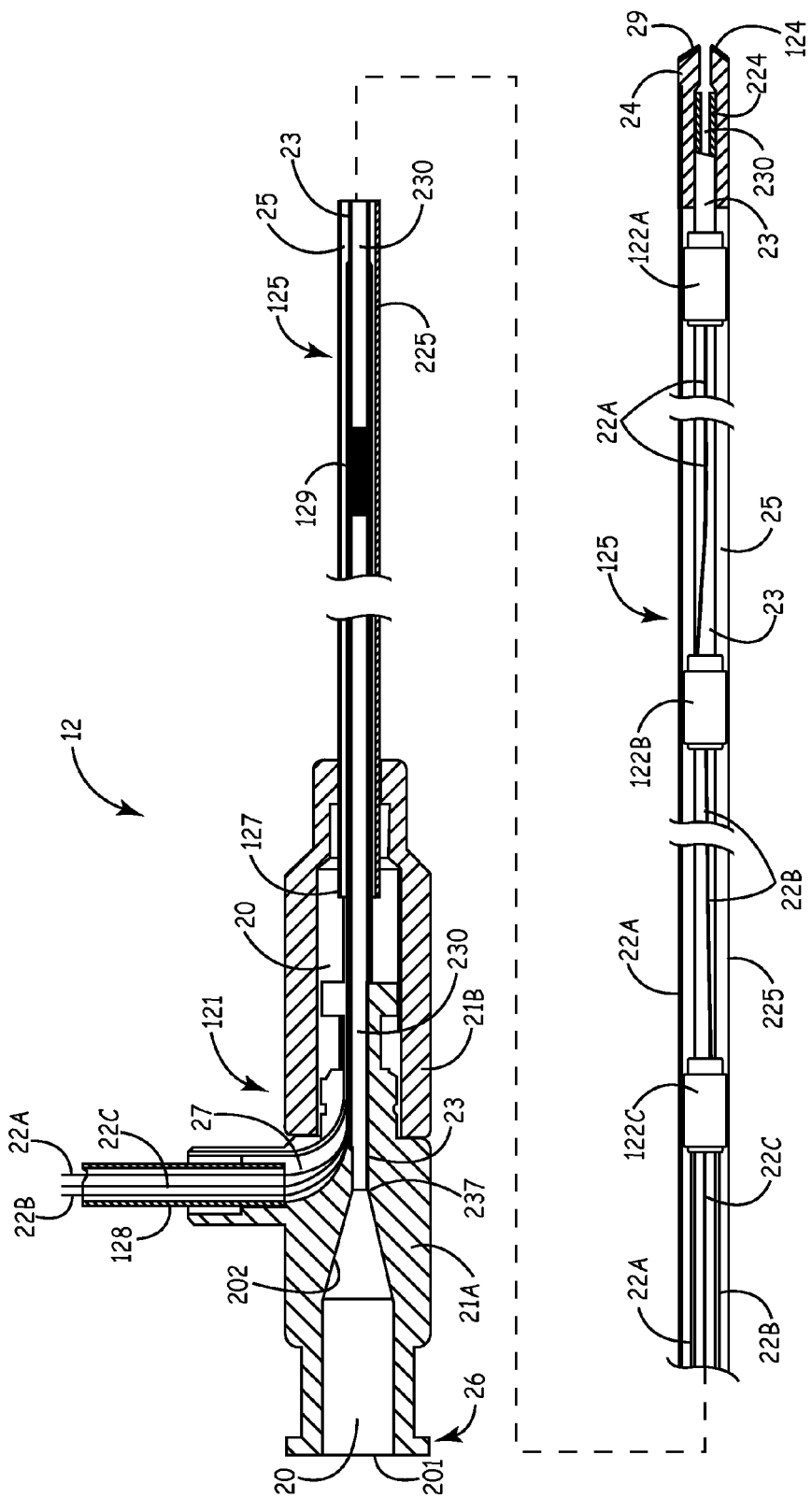
FIG. 2 is a longitudinal section view of a navigation element, from the system shown in FIG. 1, according to some embodiments of the present invention.

FIG. 2 is a longitudinal section view of navigation element 12, from system 100 shown in FIG. 1A, according to some embodiments of the present invention. FIG. 2 illustrates elongate body 125 of navigation element including an outer tube 225 extending from hub 121 to distal end 124 over receiver assemblies 122A, B, C, and an inner tube 23 extending within a lumen 25 of outer tube 225 along a length of outer tube 225 and within receiver assemblies 122A, B, C. A distal tip 24, shown terminating outer tube 225 at distal end 124, is coupled to a distal end 224 of inner tube 23 such that an inner lumen 230, formed by inner tube 23, extends out distal end 124. Lumen 230 may be used to deliver a diagnostic agent, for example a contrast agent to aid in fluoroscopic guidance. Alternately, or additionally, lumen may used to deliver a therapeutic agent, for example drugs or genetic material; one example of a modular delivery element, which can be inserted through lumen 230, for delivery of such agents is described in conjunction with FIGS. 5A-B.

FIG. 2 further illustrates each receiver assembly 122A, B, C including a respective conductor 22A, 22B and 22C extending proximally therefrom, within lumen 25 of outer tube 225, outside inner tube 23, and within proximal receiver assemblies, for example, conductor 22A within assemblies 122B, C and conductor 22B within assembly 122C; conductors 22A, B, C further extend into a lumen 20 of hub 121 and then into a channel 27, of hub 121. According to the illustrated embodiment, channel 27 extends laterally from hub lumen 20 to route conductors 22A, B, C into insulated extension 128 for coupling with connector 126 (FIGS. 1 and 4), and inner tube 23 extends within hub 121 proximally past channel 27 such that lumen 230 meets with hub lumen 20 in proximity to a hub entry 201. Entry 201 is shown including a tapered section 202 that may facilitate introduction of the aforementioned diagnostic and/or therapeutic agent into lumen 230 for delivery out distal end 124; entry 201 is further shown including a fitting 26 that may be used for coupling with a diagnostic and/or therapy delivery tool. For ease of assembly, hub 121 may be divided into two parts to facilitate formation of inner and outer assemblies for navigation element 12; for example, as illustrated in FIG. 2, inner tube 23 is coupled to a hub proximal portion 21A to form an inner assembly, and outer tube 225 is coupled to a hub distal portion 21B to form an outer assembly. It may be appreciated that space in between inner tube 23 and outer tube 225 provides a sealed environment for receiver assemblies 122A, B, C and corresponding conductors 22A, B, C, which is separate from lumen 230. According to certain embodiments of the present invention, inner tube 23 has an outer diameter between approximately 0.054 inch and approximately 0.058 inch and is extruded polyurethane having a hardness of approximately 75 D; and outer tube 225 has an inner diameter between approximately 0.063 inch and approximately 0.08 inch, and is extruded polyurethane having a hardness of approximately 55 D. Alternately outer tube 225 may be a variable stiffness braid-reinforced shaft of similar construction to those employed for some guiding catheters and known to those skilled in the art.

Figure 3C:
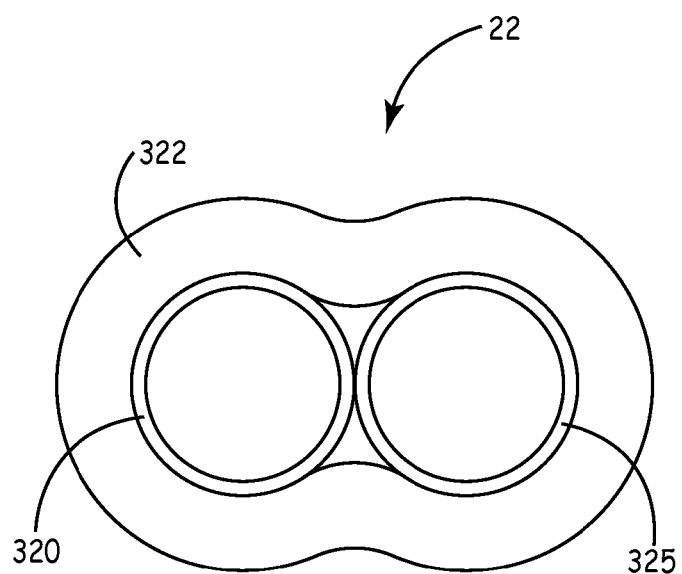
FIG. 3C is a section view, through line G-G shown in FIG. 3A.

According to some embodiments of the present invention, for visualization via fluoroscopy, distal tip 24 is radiopaque, including a radiopaque marker band, for example formed of platinum, or formed from a radiopaque material, for example a platinum-iridium alloy or a plastic loaded with barium sulfate filler. Distal tip 24 may be an electrode or may include an electrode 29, for example, formed from Platinum-Iridium or stainless steel, mounted thereon, as illustrated in FIG. 2; electrode 29 can provide electrical mapping capability to navigation element by sensing electrical activity of a surrounding environment, for example electrical depolarization of cardiac tissue adjacent tip 24. An insulated conductor for electrode 29 (not shown) extends proximally from electrode 29 to proximal end 127 of body 125 in between inner tube 23 and outer tube 225 in a similar fashion to that described for conductors 22A, B, C of receiver assemblies 122A, B, C FIGS. 3A-B are a plan view and an end view of a receiver assembly 122 for a navigation element, which may be any of receiver assemblies 122A, B, C of element 12 shown in FIGS. 1 and 2, according to some embodiments of the present invention; and FIG. 3C is a section view, through line G-G shown in FIG. 3A. FIGS. 3A-B illustrate receiver assembly including a core 30, a coiled wire, wound about core 30, forming a receiver coil 35, and a conductor 22 coupled to coil 35, in proximity to a first, or distal, end 37 of coil 35. According to an exemplary embodiment, wire forming coil 35 has a diameter ranging from approximately 0.00119 inch to approximately 0.00129 inch and is made from a copper alloy, i.e. Electrolytic Tough Pitch (ETP) Copper (CDA alloy no. 11000), having an insulative coating of polyurethane nylon over-coated with a polyvinyl butyral adhesive; the wire may be wound in approximately six layers of windings, each layer having approximately 80 turns per layer resulting in approximately 480±20 turns for coil 35 that gives receiver assembly 122 an approximate inductance of 140 μH. Core 30, for example formed from polyimide tubing having a wall thickness between approximately 0.001 inch and approximately 0.002 inch, is shown including a channel 33, formed along an exterior surface of core 30, through which conductor 22 extends from coupling with coil 35 to a second, or proximal, end 38 of coil 35 and proximally therefrom. The illustrated routing of conductor 22 through channel 33 of core beneath coil 35 may provide effective strain relief for conductor 22. Although channel 33 is shown extending in a relatively straight longitudinal direction along the core outer surface, alternate embodiments of core 30 include channels that take other paths along the core outer surface between distal end 37 and proximal end 38.

With reference to FIG. 3C, conductor 22 is shown including first and second insulated wires 320 and 325 extending alongside one another; wires 320, 325 may be formed of a copper alloy, i.e. Electrolytic Tough Pitch (ETP) Copper (CDA alloy no. 11000), having an insulative coating of polyimide and may be twisted about one another along a majority of a length of conductor 22 and held together by an overjacket of insulation 322, for example made from a perfluoroalkoxy fluoropolymer resin (PFA), as illustrated in FIG. 3C. According to an exemplary embodiment: insulated wires 320, 325 have a diameter ranging from approximately 0.0015 inch to approximately 0.004 inch; conductor 22, including overjacket 322, has a maximum width ranging from approximately 0.008 inch to approximately 0.015 inch; and wires 320, 325 have a twist rate ranging from approximately 13 to approximately 15 twists per inch in a left-handed lay orientation having a lay length between approximately 0.065 inch and approximately 0.08 inch.

According to the embodiment illustrated in FIGS. 3A-B, each wire 320, 325 includes a distal end 321 and 324, respectively, that are split apart from one another so that ends 321, 324 extend away from one another in proximity to first end 37 of coil 35; the coiled wire of receiver coil 35 is wound such that first and second ends 351 and 354 of coiled wire are both disposed in proximity to coil first end 37 for coupling with conductor wire ends 321 and 324, respectively, for example by soldering with a 60/40 tin/lead composition. Coil wire ends 351, 354 are each shown wrapped about respective conductor wire ends 321, 324 for secure junctions; the junctions, as well as conductor 22 within channel 33, may be bonded to core 30, for example with a cynoacrylate adhesive, such as Loctite 49850. It may be appreciated that core 30 supports the junctions of each coil wire end 351, 354 to the corresponding conductor wire end 321, 324 and provides for a low profile cylindrical contour of the junctions. However, it should be noted that receiver assembly 122, according to some alternate embodiments of the present invention, does not include core 30; rather an adhesive that is used to pot around the wound coil wires of coil 35 is used to support the illustrated junction with conductor 22.

An electrical resistance of assembly 122 may be between approximately 60 and approximately 150 ohms and an inductance between approximately 72 and approximately 170 μH (measured using a 1 KHz frequency, 1 Volt AC waveform). According to an exemplary embodiment of the present invention: a length of conductor 22 extending from receiver coil 35 is at least approximately 80 inches; a length of receiver coil 35 is between approximately 0.1 inch and approximately 0.16 inch, with core 30 being longer as illustrated, for example, up to approximately 0.18 inch long; an outer diameter of receiver coil 35 is no greater than approximately 0.08 inch; and a minimum breadth 391 of an inner lumen 39 of core 30 (FIG. 3B) is sufficient to accommodate inner tube 23 extending therethrough, as illustrated in FIG. 2, being between approximately 0.04 inch and approximately 0.06 inch. According to the embodiment illustrated in FIG. 2, because conductors of the receiver assemblies are routed between inner tube 23 and outer tube 225, core inner lumen 39 of receiver assembly 122 B also accommodates conductor 22A and core inner lumen 39 of receiver assembly 122C also accommodates conductors 22A and 22B.

FIG. 3A further illustrates insulation over-jacket 322 of conductor 22 terminated proximal to the junction with coil 35, to allow for the splitting apart of wires 320, 325, but extending a distance within core channel 33 beneath coil 35, for example approximately 0.06 inch, to provide some strain relief at second end 38 of coil 35 from which conductor extends. Optional additional strain relief is illustrated in the form of a strain relief tube 323, for example formed from polyimide, extending around conductor 22 for a relatively short length, for example between approximately 4.5 inches and approximately 5 inches, just proximal to coil second end 38. According to alternate embodiments, wherein the coiled wire of receiver coil 35 is potted with adhesive, tube 323 extends beneath coil, for example to a depth illustrated for over-jacket 322, to keep conductor 22 from being tacked down between coil 35 and core. It should be noted that embodiments of the present invention are not limited by the exemplary illustrated strain-relief and may include no strain relief or alternative forms.

Figure 4:
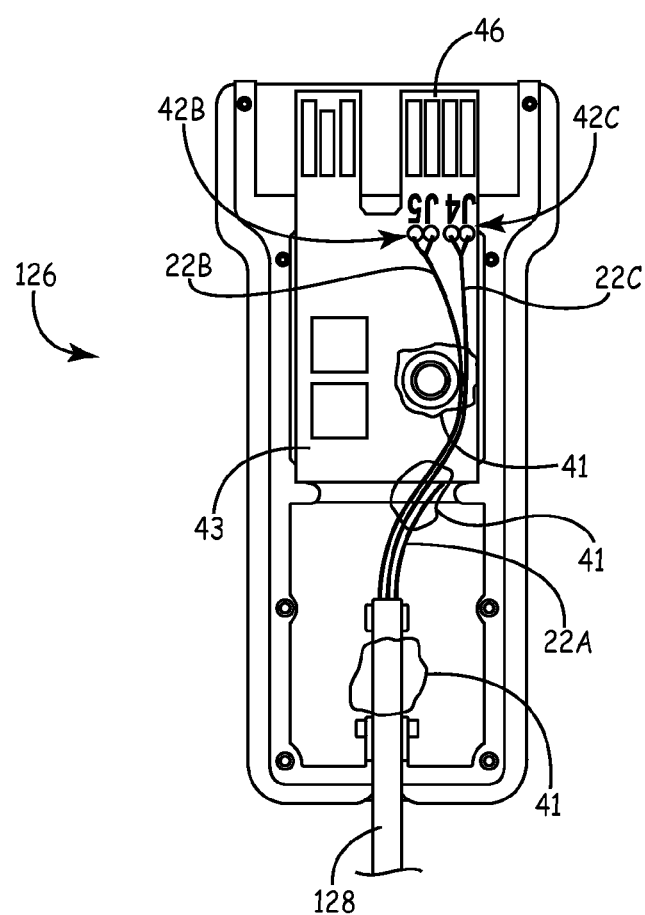
FIG. 4 is a plan view of a connector assembly beneath a cover of the connector shown in FIG. 1, per line H-H, according to some embodiments of the present invention.

Referring back to FIGS. 1 and 2, conductors 22A, B, C are shown routed from hub 121 into connector 126, via insulated extension 128. FIG. 4 is a plan view of a connector assembly beneath a cover of connector 126, per line H-H of FIG. 1, according to some embodiments of the present invention. FIG. 4 illustrates extension 128 routing conductors 22A, B, C into connector 126 and bond sites 41 where extension 128 and conductors 22A, B, C are secured within connector 126, for example with epoxy adhesive. According to the illustrated embodiment, connector 126 includes a probe board 43 to which conductors 22B and 22C are electrically coupled, for example, via soldering, at junctions 42B and 42C, respectively. Conductor 22A is shown routed to an opposite side of probe board 43 for coupling at a junction, similar to 42B, C, on the opposite side of board 43. FIG. 4 further illustrates an extension of probe board 43 on which contacts 46 are formed for electrical coupling of conductors 22A, B, C with an analysis system so that current induced in receiver assemblies 122A, B, C can be received by the analysis system to create a visual map for navigation, as previously described.

Figure 5B:
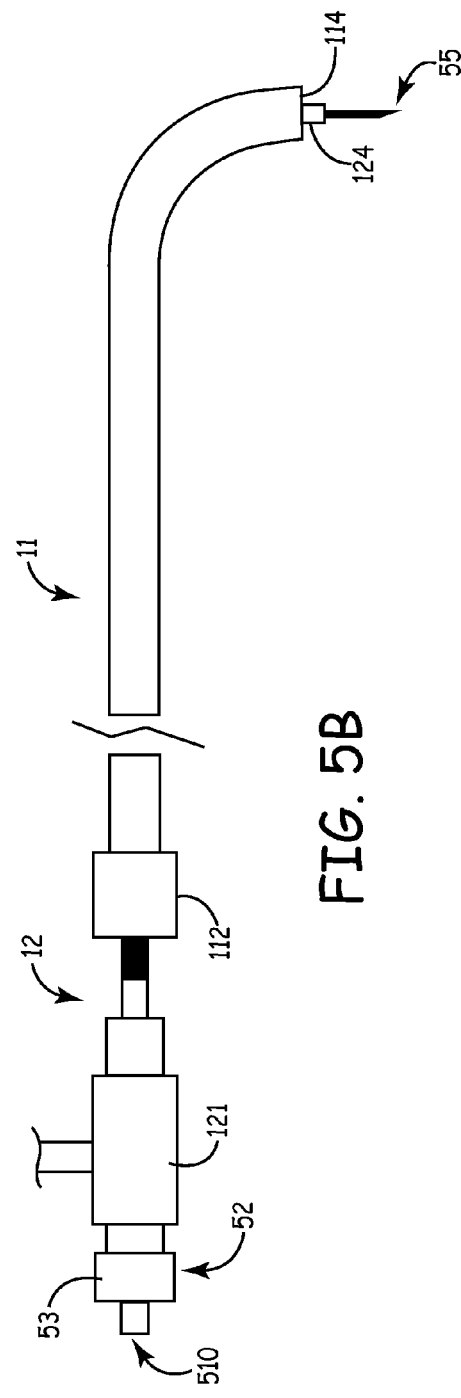

FIGS. 5A-B are plan views of modular system 100, further including another modular element and depicting assembly thereof according to further embodiments of the present invention. As previously described in conjunction with FIG. 1, navigation element 12 is inserted within catheter 11 to aid an operator in navigating catheter 11 within a body of a patient to a target site; FIG. 5A illustrates navigation element 12 positioned such that distal end 124 of navigation element extends out distal end 114 of catheter 11, and most distal receiver assembly 122A is located in proximity to distal end 114 of catheter 11. A hub 112 terminating proximal end 117 of catheter 11 may include a Tuohy-Borst valve to secure element 12 within catheter 11 and prevent backflow of bodily fluids through the catheter lumen during navigation within the body of the patient. According to an exemplary embodiment of the present invention, receiver assemblies 122A, B, C are spaced approximately 5 centimeters from one another, center to center. As previously discussed, bend 111 of catheter 11 may be pre-formed so that know fixed dimensions of bend could be used to interpolate between signals from receiver assemblies 122A, B, C; alternately, if catheter 11 includes an element, for example a pull-wire, to actively bend the distal portion thereof, bending properties of catheter 11 could be used to interpolate a shape of the distal portion between receiver assemblies 122A, B, C. Electrode 29, shown at distal end 124, may be used to map electrical activity, as previously described, providing another piece of information for navigation.

FIGS. 1, 2 and 5A further illustrate navigation element 12 including an optional marker band 129 formed about body 125, in proximity to hub 121, at a location to correspond to a particular catheter length. According to the illustrated embodiment, when a particular feature of element 12 is positioned at a predetermined spot with respect to catheter 11, for example distal end 124 protruding from distal end 114 of catheter or one of distal receiver assemblies 122A, B, C in proximity to distal end 114, marker 129 is located at a predetermined spot corresponding to a proximal end of catheter hub 112, for example adjacent a Tuohy-Borst valve. Such a visual indicator may be a quick way for an operator to set up system 100 in situ, that is inserting navigation element 12 into catheter 11 after catheter 11 has already been inserted into a body of a patient.

Figure 6:
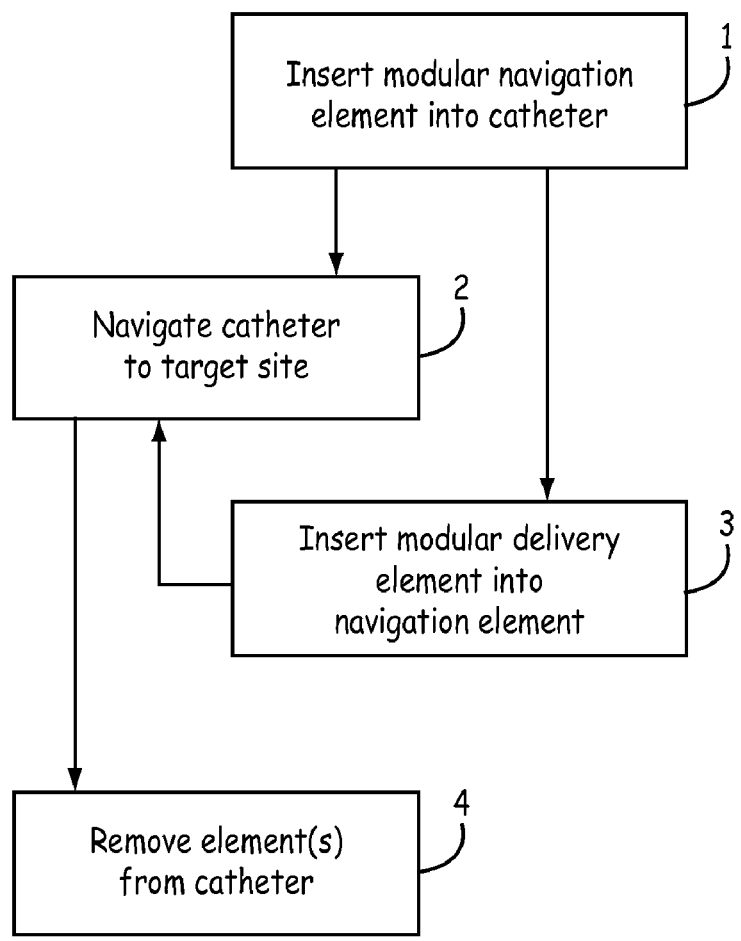
FIG. 6 is a flowchart outlining methods according to the present invention

FIG. 6 is a flowchart outlining methods according to the present invention and FIG. 5A further illustrates a modular delivery element 50 directed for insertion, per arrow B, into navigation element 12 (step 3, FIG. 6), which has been assembled within catheter 11 (step 1, FIG. 6), as previously described. FIG. 6 shows alternative method sequences: one in which catheter 11 is navigated to the target site (step 2) before inserting delivery element 50 into catheter (step 3), another in which step 3 precedes step 2, and another in which step 3 is not included.

According to the embodiment illustrated in FIG. 5A, delivery element 50 includes an elongate body 51 terminated at a distal end with a piercing tip or needle 55, and terminated at a proximal end with a hub 52. Hub 52 includes a fitting 53, for example a luer lock type, for joining delivery element 50 to mating fitting 26 of navigation element hub 121, after element 50 has been inserted therein, as illustrated in FIG. 5B. FIG. 5B further illustrates an entry 510 leading into a lumen (not shown) of delivery element 50 for delivery of therapeutic agents out through piercing tip 55, which is shown extending from distal end 124 of navigation element 12. One suitable construction of modular delivery element 50 is described in commonly assigned patent application publication number 2005/0277889, entitled "Modular Medical Injection System", relevant parts of which are hereby incorporated by reference.

According to some embodiments of the present invention, once assembly 100 has been navigated to a target site (step 2, FIG. 6) and delivery element 50 inserted within navigation element 12 (step 3, FIG. 6), needle 55 may be positioned with respect to navigation element 12 according to an adjustment of the junction between delivery element hub 52 and navigation element hub 121; the position of needle 55 may be preset according to the hub junction and a length of body 51, with respect to a length of navigation element 12, or may be adjustable within a preset range at the hub junction. In cases where catheter 11 is a steerable catheter, because navigation element 12 is independent of catheter 11, element 12 will not compress with the steerable catheter shaft so that a depth correction for needle tip 55 according to the compression of catheter 11 is not necessary. After positioning system 100 at a target site, inserting needle 55, to extend out from distal end 124, and delivering an agent through needle 55, navigation element 12 and delivery element 50 may be removed from catheter 11 (step 4, FIG. 6) to make way for delivery of a device through catheter 11 to the target site, for example an implantable medical device or a diagnostic device.

In the foregoing detailed description, the invention has been described with reference to specific embodiments. However, it may be appreciated that various modifications and changes can be made without departing from the scope of the invention as set forth in the appended claims.

The invention claimed is:

1. An electromagnetic receiver assembly for a navigation element of a therapy delivery system, the assembly comprising:
   a receiver coil including a proximal end, a distal end and a coiled wire, the coiled wire includes a first wire end and a second wire end, both wire ends of the coiled wire disposed in proximity to the receiver coil distal end; and
   a conductor including a first insulated wire extending alongside a second insulated wire, the first and second wires of the conductor each include an end, the first and second conductor wire ends extending away from one another in proximity to the receiver coil proximal end and the first and second insulated wires of the conductor are respectively wrapped about the first and second wire ends of the coiled wire in proximity to the distal end of the receiver coil and extending within the receiver coil to the proximal end of the receiver coil and outward from the proximal end of the receiver coil.

2. The assembly of claim 1, further comprising a core about which the coiled wire is wound, and wherein the conductor extends in between the coil and the core.

3. The assembly of claim 2, wherein the core includes a length that is within approximately 0.01 inch and 1 inch of the length of the coil.

4. The assembly of claim 2, wherein the core includes a channel extending along an outer surface thereof and the conductor extends within the channel.

5. The assembly of claim 2, wherein the core includes a longitudinally extending lumen and a minimum breadth of the lumen is greater than approximately 0.04 inch.

6. The assembly of claim 1, wherein an outer diameter of the receiver coil is no greater than approximately 0.08 inch.

7. The assembly of claim 1, wherein the conductor includes a strain-relief tubing extending around the first wire and the second wire and along a length of the conductor that extends away from the second end of the coil.

8. The assembly of claim 1, wherein a length of the conductor is greater than approximately 80 inches.

* * * * *